United States Patent
Li

(10) Patent No.: US 10,575,730 B2
(45) Date of Patent: Mar. 3, 2020

(54) ULTRA WIDE FIELD FUNDUS IMAGING SYSTEM

(71) Applicant: SUZHOU MICROCLEAR MEDICAL INSTRUMENTS CO., LTD., Suzhou, Jiangsu Province (CN)

(72) Inventor: Chaohong Li, Suzhou (CN)

(73) Assignee: SUZHOU MICROCLEAR MEDICAL INSTRUMENTS CO., LTD., Suzhou, Jiangsu Province (CN)

( * ) Notice: Subject to any disclaimer, the term of this patent is extended or adjusted under 35 U.S.C. 154(b) by 17 days.

(21) Appl. No.: 15/768,544

(22) PCT Filed: Nov. 24, 2016

(86) PCT No.: PCT/CN2016/107011
§ 371 (c)(1),
(2) Date: Apr. 14, 2018

(87) PCT Pub. No.: WO2018/086157
PCT Pub. Date: May 17, 2018

(65) Prior Publication Data
US 2019/0082956 A1    Mar. 21, 2019

(30) Foreign Application Priority Data
Nov. 9, 2016 (CN) .......................... 2016 1 0984986

(51) Int. Cl.
*A61B 3/14* (2006.01)
*A61B 3/12* (2006.01)
(Continued)

(52) U.S. Cl.
CPC .............. *A61B 3/12* (2013.01); *A61B 3/0016* (2013.01); *A61B 3/103* (2013.01); *A61B 3/1025* (2013.01);
(Continued)

(58) Field of Classification Search
CPC ........... A61B 3/14; A61B 3/0025; A61B 3/12; A61B 3/102; A61B 3/0008
(Continued)

(56) References Cited

U.S. PATENT DOCUMENTS 5,784,148 A * 7/1998 Heacock .............. A61B 3/1025
351/206
5,815,242 A * 9/1998 Anderson ............ A61B 3/1025
351/205
(Continued)

FOREIGN PATENT DOCUMENTS

CN    102008288 A    4/2011
CN    102429638 A    5/2012
(Continued)

*Primary Examiner* — Mohammed A Hasan
(74) *Attorney, Agent, or Firm* — Cheng-Ju Chiang

(57) ABSTRACT

An ultra wide field fundus imaging system comprises a photosource, an optical splitter, a scanning assembly, a curved reflector, a probe pinhole and an imaging assembly. The scanning assembly includes a first scanning mirror scanning along a first direction and a second scanning mirror scanning along a second direction. The light emitted by the photosource passes through the optical splitter, then successively is reflected by the first scanning mirror, the curved reflector, the second scanning mirror and the curved reflector, and then enters in the fundus; the light entering the fundus is reflected by the retina and then successively is reflected by the curved reflector, the second scanning mirror, the curved reflector, the first scanning mirror and then returned to the optical splitter; the light is reflected by the optical splitter and passes through the probe pinhole, finally the light enters in the imaging assembly. Compared with the prior art, the ultra wide field fundus imaging system realizes fundus imaging by total reflection and can effectively avoid ghost images caused by lens module imaging to improve the imaging quality. Since the curvature of the curved reflector (Continued)

is gradually changed, so the light reflected by the curved reflector can enter in the fundus at a larger incident angle to achieve wide field imaging.

10 Claims, 1 Drawing Sheet

(51) Int. Cl.
| | |
|---|---|
| *G02B 26/10* | (2006.01) |
| *G02B 27/14* | (2006.01) |
| *G02B 27/00* | (2006.01) |
| *G02B 5/10* | (2006.01) |
| *A61B 3/00* | (2006.01) |
| *A61B 3/10* | (2006.01) |
| *A61B 3/103* | (2006.01) |

(52) U.S. Cl.
CPC .................. *A61B 3/14* (2013.01); *G02B 5/10* (2013.01); *G02B 26/101* (2013.01); *G02B 27/0081* (2013.01); *G02B 27/141* (2013.01); *G02B 27/144* (2013.01)

(58) Field of Classification Search
USPC .......................................................... 351/206
See application file for complete search history.

(56) References Cited

U.S. PATENT DOCUMENTS

| | | | |
|---|---|---|---|
| 5,949,520 A * | 9/1999 | Heacock | A61B 3/1025 351/221 |
| 8,783,868 B2 * | 7/2014 | Qiu | A61B 3/18 351/206 |
| 2014/0340635 A1 | 11/2014 | Oyaizu | |
| 2015/0216408 A1* | 8/2015 | Brown | A61B 3/1015 351/206 |

FOREIGN PATENT DOCUMENTS

| | | |
|---|---|---|
| CN | 102641115 A | 8/2012 |
| WO | 2014/020966 A1 | 2/2014 |

* cited by examiner

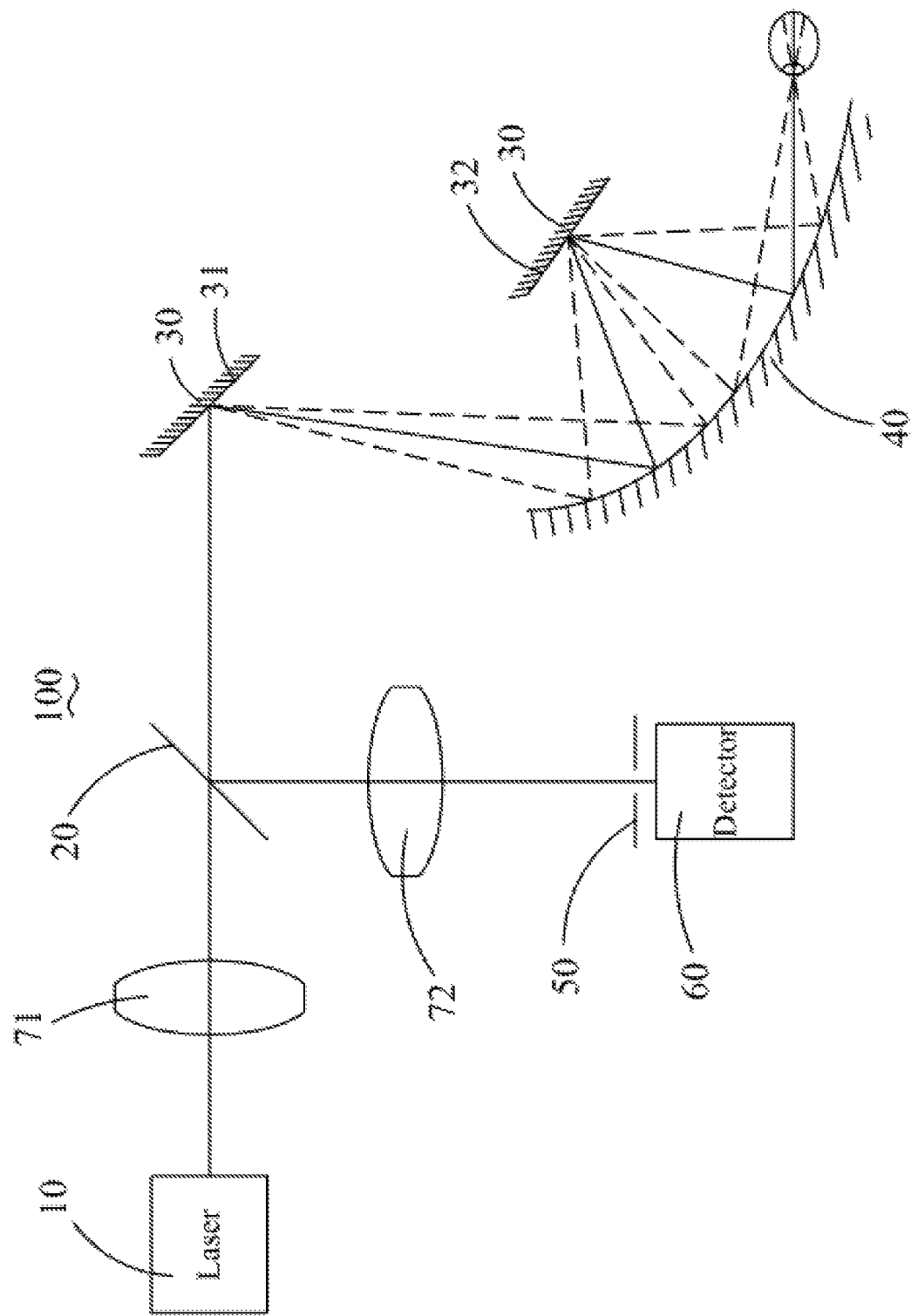

ULTRA WIDE FIELD FUNDUS IMAGING SYSTEM

CROSS-REFERENCE TO RELATED APPLICATIONS

This application claims priority to Chinese Application Serial No. 201610984986.X, filed Nov. 9, 2016, the disclosures of which are hereby incorporated by reference in their entirety.

TECHNICAL FIELD

The present invention generally relates to fundus imaging system, and more particularly to a total reflection confocal scanning fundus imaging system.

BACKGROUND

The fundus camera belongs to medical imaging field, is used for obtaining human retina images to assist medical staff checking fundus diseases and judging the condition of other organs. Because only fundus veins can directly observe through body surface, the medical staff can check the optic nerve, retina, choroid and refractive media in the fundus by the fundus camera to identify the fundus condition, at the same time, the fundus camera can assist to diseases diagnosis and disease judgment for other organ systems, such as: the retina can be used to detect cerebral infarction, stroke, cerebral arteriosclerosis, brain tumor, diabetes, nephropathy, hypertension, retinopathy of prematurity, glaucoma and age-related macular degeneration and so on. The earlier detection of these diseases is more conducive to clinical treatment. Currently, fundus camera is commonly used in clinical screening of fundus diseases, become an indispensable medical device.

Currently, the fundus camera mainly through the lens module to achieve fundus imaging. However, the lens module likely to reflect the illumination light to form a ghost image, affecting the imaging quality. In addition, the imaging field of the lens module imaging system is small and can not satisfy the medical staff's demand for wide field imaging.

In consideration of the above problems, there is a need to provide a new type fundus imaging system to solve the above problems.

SUMMARY OF INVENTION

The aim of the present invention is to provide an ultra wide field fundus imaging system, which can effectively avoid ghost images caused by lens module imaging and can achieve wide field imaging to improve the imaging quality.

In order to achieve the aim of the invention, the present invention provides an ultra wide field fundus imaging system comprises a photosource, an optical splitter, a scanning assembly, a probe pinhole and an imaging assembly; the scanning assembly includes a first scanning mirror scanning along a first direction and a second scanning mirror scanning along a second direction; wherein the ultra wide field fundus imaging system further comprises a curved reflector arranged opposite to the scanning assembly; the light emitted by the photosource passes through the optical splitter, then successively is reflected by the first scanning mirror, the curved reflector, the second scanning mirror and the curved reflector, and then enters in the fundus; the light entering the fundus is reflected by the retina and then successively is reflected by the curved reflector, the second scanning mirror, the curved reflector, the first scanning mirror and then returned to the optical splitter; the light is reflected by the optical splitter and passes through the probe pinhole, finally the light enters in the imaging assembly.

As a preferred embodiment of the present invention, the curved reflector is ellipsoid-shaped, and the concave surface of the curved reflector is reflection surface.

As a preferred embodiment of the present invention, the trajectory of the light reflected by the first scanning mirror to the curved reflector on the curved reflector is parabola; the trajectory of the light reflected by the second scanning mirror to the curved reflector on the curved reflector is parabola.

As a preferred embodiment of the present invention, a rotation angle of the first scanning mirror rotating in a unit time is first scanning angle; the trajectory of the light reflected by the first scanning mirror to the curved reflector on the curved reflector in a unit time is first trajectory line, the tangent line of the first trajectory line at the starting point and the tangent line at the ending point of the first trajectory line forms first trajectory angle; the difference between the first scanning angle and the first trajectory angle is a constant value.

As a preferred embodiment of the present invention, a rotation angle of the second scanning mirror rotating in a unit time is second scanning angle; the trajectory of the light reflected by the second scanning mirror to the curved reflector on the curved reflector in a unit time is second trajectory line, the tangent line of the second trajectory line at the starting point and the tangent line at the ending point of the second trajectory line forms second trajectory angle; the difference between the second scanning angle and the second trajectory angle is a constant value.

As a preferred embodiment of the present invention, the optical splitter is half-reflection pellicle mirror.

As a preferred embodiment of the present invention, the optical splitter is hollow reflector.

As a preferred embodiment of the present invention, the optical splitter is dichroic mirror.

As a preferred embodiment of the present invention, the first scanning mirror is resonant scanning mirror or rotating polygon scanning mirror; the second scanning mirror is mechanical scanning mirror.

As a preferred embodiment of the present invention, a focusing lens is provided between the optical splitter and the probe pinhole.

Compared with the prior art, the benefits of the prevent invention as follows: the ultra wide field fundus imaging system realizes fundus imaging through total reflection and can effectively avoid ghost images caused by lens module imaging to improve the imaging quality. Since the curvature of the curved reflector 40 is gradually changed, so the light reflected by the curved reflector 40 can enter in the fundus at a larger incident angle (achieving 100°~180° fundus perspective imaging), thereby achieving wide field imaging.

BRIEF DESCRIPTION OF DRAWINGS

FIG. 1 is a schematic view of an ultra wide field fundus imaging system of the present invention.

DESCRIPTION OF EMBODIMENTS

In order to clear the purpose, the technical scheme and the advantages of the invention, reference will now be made to the drawing FIGURES to describe the embodiments of the present disclosure in detail.

Referring to FIG. 1, the present invention an ultra wide field fundus imaging system 100 comprises a photosource 10, an optical splitter 20, a scanning assembly 30, a curved reflector 40 arranged opposite to the scanning assembly 30, a probe pinhole 50 and an imaging assembly 60. The scanning assembly 30 includes a first scanning mirror 31 scanning along a first direction and a second scanning mirror 32 scanning along a second direction; the first direction is orthogonal to the second direction. The light emitted by the photosource 10 passes through the optical splitter 20, then reflected by the first scanning mirror 31, the curved reflector 40, the second scanning mirror 32 and the curved reflector 40 respectively, and then enters in the fundus. The light entering the fundus is reflected by the retina and then reflected by the curved reflector 40, the second scanning mirror 32, the curved reflector 40, the first scanning mirror 31 respectively, and then returned to the optical splitter 20; the light is reflected by the optical splitter 20 and passes through the probe pinhole 50, finally the light enters in the imaging assembly 60.

Referring to FIG. 1, the photosource 10 may be single-wavelength laser, or multi-wavelength compound light, or natural light. The optical splitter 20 may be a dichroic mirror, or a half-reflection pellicle mirror, or hollow reflector. A collimator lens 71 is disposed between the photosource 10 and the optical splitter 20, can achieve that the light emitted by the photosource 10 emitted to the optical splitter 20 in the form of parallel light. The first scanning mirror 31 may be resonant scanning mirror or rotating polygon scanning mirror. The second scanning mirror 32 is mechanical scanning mirror or other kind of large-angle rotation scanning mirror. The curved reflector 40 is a spherical mirror or an ellipsoidal mirror, and the concave surface of the curved reflector 40 is reflection surface. A focusing lens 72 is disposed between the probe pinhole 50 and the optical splitter 20. The imaging assembly 60 is an image sensor.

Compared with the prior art, the present invention ultra wide field fundus imaging system realizes fundus imaging through total reflection and can effectively avoid ghost images caused by lens module imaging to improve the imaging quality. Since the curvature of the curved reflector 40 is gradually changed, so the light reflected by the curved reflector 40 can enter in the fundus at a larger incident angle (achieving 100°~180° fundus perspective imaging), thereby achieving wide field imaging. The ultra wide field fundus imaging system 100 can be applied to autofluorescent retinal angiography, choroidal angiography, near-infrared imaging, fundus color imaging and so on.

In addition, in order to further improve the imaging quality, the curved reflector 40 can also be designed as follows:

The trajectory of the light reflected by the first scanning mirror 31 to the curved reflector 40 on the curved reflector 40 is parabola; the trajectory of the light reflected by the second scanning mirror 32 to the curved reflector 40 on the curved reflector 40 is parabola.

In addition, in order to achieve evenly scanning, the curved reflector 40 can also be designed as follows:

A rotation angle of the first scanning mirror 31 rotating in a unit time is first scanning angle. The trajectory of the light reflected by the first scanning mirror 31 to the curved reflector 40 on the curved reflector 40 in a unit time is first trajectory line, the tangent line of the first trajectory line at the starting point and the tangent line at the ending point of the first trajectory line forms first trajectory angle. The difference between the first scanning angle and the first trajectory angle is a constant value.

A rotation angle of the second scanning mirror 32 rotating in a unit time is second scanning angle. The trajectory of the light reflected by the second scanning mirror 32 to the curved reflector 40 on the curved reflector 40 in a unit time is second trajectory line, the tangent line of the second trajectory line at the starting point and the tangent line at the ending point of the second trajectory line forms second trajectory angle. The difference between the second scanning angle and the second trajectory angle is a constant value.

Even though numerous characteristics and advantages of preferred and exemplary embodiments have been set out in the foregoing description, together with details of the structures and functions of the embodiments, the disclosure is illustrative only; and the general technical personnel in this field should understand that the technical plan of the invention can be modified or equivalent instead of being divorced from the spirit and scope of the technical scheme of the invention.

What is claimed is:

1. An ultra wide field fundus imaging system comprises a photosource, an optical splitter, a scanning assembly, a probe pinhole and an imaging assembly; said scanning assembly includes a first scanning mirror scanning along a first direction and a second scanning mirror scanning along a second direction; wherein said ultra wide field fundus imaging system further comprises a curved reflector arranged opposite to said scanning assembly; the light emitted by said photosource passes through said optical splitter, then successively is reflected by said first scanning mirror, said curved reflector, said second scanning mirror and said curved reflector, and then enters in the fundus; the light entering the fundus is reflected by the retina and then successively is reflected by said curved reflector, said second scanning mirror, said curved reflector, said first scanning mirror and then returned to said optical splitter; the light is reflected by said optical splitter and passes through said probe pinhole, finally the light enters in said imaging assembly.

2. The ultra wide field fundus imaging system according to claim 1, wherein said curved reflector is ellipsoid-shaped, and the concave surface of said curved reflector is reflection surface.

3. The ultra wide field fundus imaging system according to claim 1, wherein the trajectory of the light reflected by said first scanning mirror to said curved reflector on said curved reflector is parabola; the trajectory of the light reflected by said second scanning mirror to said curved reflector on said curved reflector is parabola.

4. The ultra wide field fundus imaging system according to claim 1, wherein a rotation angle of said first scanning mirror rotating in a unit time is first scanning angle; the trajectory of the light reflected by said first scanning mirror to said curved reflector on said curved reflector in a unit time is first trajectory line, the tangent line of said first trajectory line at the starting point and the tangent line at the ending point of said first trajectory line forms first trajectory angle; the difference between said first scanning angle and said first trajectory angle is a constant value.

5. The ultra wide field fundus imaging system according to claim 1, wherein a rotation angle of said second scanning mirror rotating in a unit time is second scanning angle; the trajectory of the light reflected by said second scanning mirror to said curved reflector on said curved reflector in a unit time is second trajectory line, the tangent line of said second trajectory line at the starting point and the tangent line at the ending point of said second trajectory line forms second trajectory angle; the difference between said second scanning angle and said second trajectory angle is a constant value.

6. The ultra wide field fundus imaging system according to claim 1, wherein said optical splitter is half-reflection pellicle mirror.

7. The ultra wide field fundus imaging system according to claim 1, wherein said optical splitter is hollow reflector.

8. The ultra wide field fundus imaging system according to claim 1, wherein said optical splitter is dichroic mirror.

9. The ultra wide field fundus imaging system according to claim 1, wherein said first scanning mirror is resonant scanning mirror or rotating polygon scanning mirror; said second scanning mirror is mechanical scanning mirror.

10. The ultra wide field fundus imaging system according to claim 1, wherein a focusing lens is provided between said optical splitter and said probe pinhole.

* * * * *